United States Patent [19]
Zebuhr

[11] Patent Number: 5,762,078
[45] Date of Patent: Jun. 9, 1998

[54] FLOSSER HEAD FOR A TOOTHBRUSH DRIVER

[75] Inventor: William H. Zebuhr, Nashua, N.H.

[73] Assignee: Dynaproducts, Inc., Nashua, N.H.

[21] Appl. No.: 621,230

[22] Filed: Mar. 25, 1996

[51] Int. Cl.$^6$ ............................................ A61C 15/00
[52] U.S. Cl. .................... 132/322; 132/323; 132/324; 132/325
[58] Field of Search .......................... 132/322, 323, 132/324, 325, 326, 327, 328, 329; 433/118, 119

[56] References Cited

U.S. PATENT DOCUMENTS

| | | | |
|---|---|---|---|
| 2,467,221 | 4/1949 | Pastl | 132/92 |
| 3,421,524 | 1/1969 | Waters | 132/92 |
| 3,534,745 | 10/1970 | Waters | 132/322 |
| 3,667,483 | 6/1972 | McCabe | 132/92 |
| 3,759,274 | 9/1973 | Warner | 132/92 R |
| 3,799,177 | 3/1974 | Bragg | 132/92 |
| 3,847,167 | 11/1974 | Brien | 132/92 R |
| 3,847,168 | 11/1974 | Schlegel | 132/92 R |
| 3,886,956 | 6/1975 | Cash | 132/91 |
| 4,014,354 | 3/1977 | Garrett | 132/90 |
| 4,235,253 | 11/1980 | Moore | 132/92 R |
| 4,245,658 | 1/1981 | Lecouturier | 132/92 A |
| 4,307,740 | 12/1981 | Florindez et al. | 132/92 R |
| 4,326,549 | 4/1982 | Hinding | 132/92 R |
| 4,338,957 | 7/1982 | Meibauer | 132/91 |
| 4,458,702 | 7/1984 | Grollimund | 132/92 A |
| 4,586,521 | 5/1986 | Urso | 132/92 R |
| 4,605,025 | 8/1986 | McSpadden | 132/92 R |
| 4,706,695 | 11/1987 | Urso | 132/92 R |
| 4,880,382 | 11/1989 | Moret et al. | 433/118 |
| 5,000,684 | 3/1991 | Odrich | 433/125 |
| 5,016,660 | 5/1991 | Boggs | 132/322 |
| 5,069,233 | 12/1991 | Ritter | 132/322 |
| 5,085,236 | 2/1992 | Odneal et al. | 132/322 |
| 5,176,157 | 1/1993 | Mazza | 132/322 |
| 5,188,133 | 2/1993 | Romanus | 132/325 |
| 5,207,773 | 5/1993 | Henderson | 132/322 |
| 5,279,314 | 1/1994 | Poulos et al. | 132/322 |
| 5,323,796 | 6/1994 | Urso | 132/322 |
| 5,343,883 | 9/1994 | Murayama | 433/118 |
| 5,450,866 | 9/1995 | Wang et al. | 132/324 |
| 5,495,863 | 3/1996 | Bergman | 132/326 |
| 5,579,786 | 12/1996 | Wolk et al. | 132/322 |
| 5,606,984 | 3/1997 | Gao | 132/325 |
| 5,647,385 | 7/1997 | Zebuhr | 132/322 |

OTHER PUBLICATIONS

Sales brochure by Oralgiene, "A Scientific Breakthrough in Dental Hygiene", at least by Dec., 1995.

Primary Examiner—Gene Mancene
Assistant Examiner—Pedro Philogene
Attorney, Agent, or Firm—Brooks & Kushman P.C.

[57] ABSTRACT

The present invention comprises a flosser head (16), detachably connectable to a motorized toothbrush driver (12). A fork portion (20) of the head includes a pair of spaced tines (24) for supporting a movable floss span (22) therebetween. Floss supply and take-up spools (30, 32) are rotatably mounted to the head for replacing the span. A ratchet (42) is arranged to drive the take-up spool by translation of relative motion between the driver and head or the driver and fork, thereby progressively advancing the span. When actuated, the driver reciprocates the fork, or the entire head, for flossing teeth and for continuously replacing the span. The flosser head is interchangeable with a toothbrush head on the driver, so the combination is a comprehensive dental cleaner.

19 Claims, 2 Drawing Sheets

5,762,078

FLOSSER HEAD FOR A TOOTHBRUSH DRIVER

TECHNICAL FIELD

The present invention relates to dental hygiene devices and more particularly to hygiene devices having power driven means for reciprocating a floss span.

BACKGROUND

Most adults have some degree of gum disease. In an advanced form, the ailment accounts for about three quarters of lost teeth. Unhealthy gums can also lead to other health problems including serious infections.

Disease of the gums can be avoided by removal of plaque, especially from under the gum line. Brushing, alone, is not sufficient because it does not clean under the gum line between teeth. Consumer organizations have tested the available plaque removing products, including the high tech powered brushes. They report that the most important aspect of proper dental hygiene is flossing.

Proper flossing by hand, however, is an arduous and loathsome regimen. It requires dexterity and some degree of skill to properly manipulate the floss to clean all the interdental surfaces down to the attached gingiva. Dexterous people find flossing tedious and it is exceedingly difficult for the nondexterous. Consequently, an estimated 90 percent of adults have some degree of the disease.

A properly designed motor-driven dental cleaner is, therefore, needed to reduce the amount of tedious work, perseverance, and dexterity required for proper dental hygiene. The present invention achieves the desired goals.

SUMMARY

The present invention comprises a flosser head, detachably connectable to the handle of a motorized toothbrush driver. A fork portion of the head includes a pair of spaced tines for supporting a movable floss span therebetween. Floss supply and take-up spools of a floss span replacing system are rotatably mounted to the head for replacing the span. A ratchet system is arranged to drive the take-up spool by translation of relative motion between the driver and head or the driver and fork, thereby progressively advancing the span. When actuated, the driver reciprocates the fork, or the entire head, for flossing teeth and for continuously replacing the span. The flosser head is interchangeable with a toothbrush head on the driver, so the combination is a comprehensive dental cleaner.

BRIEF DESCRIPTION OF THE DRAWINGS

The accompanying drawings in combination with the description herewith, illustrate features and advantages of the invention. Like reference numerals in different views refer to the same parts. The drawings are intended to illustrate principles of the invention and are not necessarily to scale.

DESCRIPTION OF PREFERRED EMBODIMENTS

Figure 1:
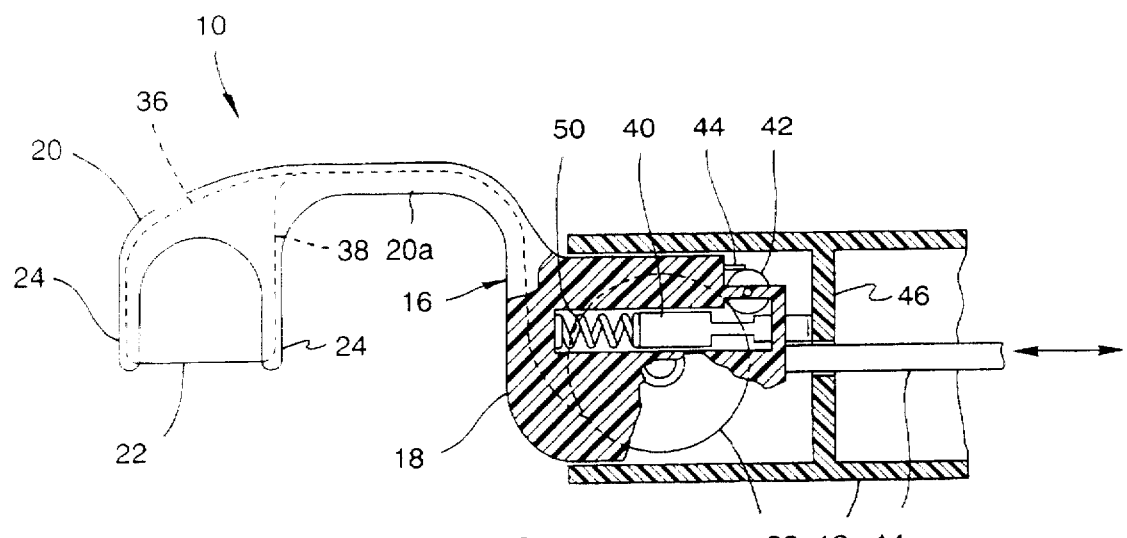
FIG. 1 is a side view, in section, of a preferred embodiment of a flosser head constructed in accordance with the invention and connected to a driver.
Figure 2:
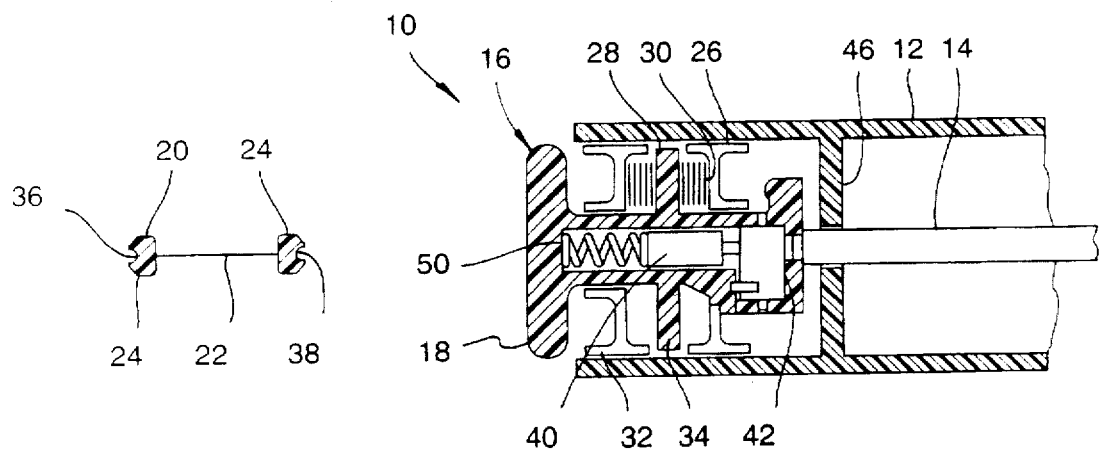
FIG. 2 is top view, in section, of the flosser head of FIG. 1.
Figure 3:
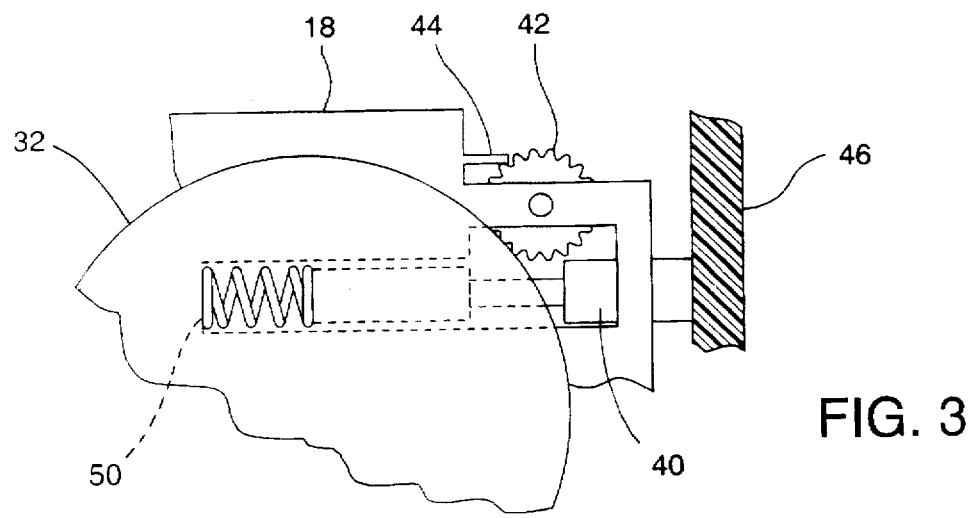
FIG. 3 is an expanded fragmental side view of the ratchet system of the flosser head of FIG. 1.

FIGS. 1–3 show a preferred embodiment of a dental cleaner 10 embodying principles of the subject invention. Included is a handle assembly 12 which is a conventional motorized toothbrush driver. A drive shaft 14 reciprocates axially relative to handle assembly 12 when a motor (not shown) housed within handle assembly 12 is energized.

A flosser head assembly 16, having a frame 18, is detachably connectable to handle assembly 12 by receiving shaft 14 in a bore within frame 18. The frame 18 is retained on drive shaft 14 by a conventional retainer (not shown). When connected to handle assembly 12, flosser head assembly 16 is rotatable about shaft 14.

Frame 18 includes a floss fork 20 for movably supporting a floss span 22 between fork tines 24. Floss fork 20 has a bend or arch 20a in the fork for reaching teeth in the back of the mouth. Floss span 22 is supplied by a floss supply spool 26 which is rotatably supported on a post 28 extending laterally from frame 18. Floss span 22 is longitudinally aligned with handle assembly 12, wherein the fork 20 can pivot about span 22 and the longitudinal axis of the entire dental cleaner 10.

An inner end of a torsion spring 30, housed in a hub of spool 26, is fixed to post 28. An outer portion of spring 30 is friction-fitted in the spool hub to form a clutch. Thus, spool 26 can slip around spring 30 if a force, rotating spool 26, exceeds friction resistance between spring 30 and spool 26.

On an opposite side of frame 18, a floss take-up spool 32 is rotatably supported on a post 34 extending laterally, opposite post 28.

Floss, drawn from supply spool 26, follows a guide groove 36, spans between tines 24, returns through guide groove 38, and winds on take-up spool 32. Floss is drawn through the described route when take-up spool 32 is driven to rotate.

A system for driving take-up spool 32 includes a ratchet wheel 42 (best seen in FIG. 3) rotatably supported on frame 18 and drivingly engaged with a rim of take-up spool 32. Ratchet wheel 42 is in friction contact with spool 32 to drive the latter when wheel 42 is rotated.

A drive pin 40, for driving ratchet wheel 42, has a portion slidably supported in a bore within frame 18. Pin 40 comprises two piston-like end portions fixedly connected by a slender mid portion. A mesial corner of one of the piston-like portions drivingly engages ratchet wheel 42. A pawl 44, supported on frame 18, also engages ratchet wheel 42 to prevent reverse rotation thereof.

An end portion of pin 40 extends posteriorly of frame 18 to engage an anterior wall 46 of handle assembly 12. Drive pin 40 is urged toward wall 46 by a loaded return spring 50 contained in a dead end portion of the bore that supports pin 40.

When drive shaft 14 reciprocates, flosser head assembly 16 reciprocates along with shaft 14. Pin 40, however, remains engaged with wall 46 urged by spring 50. The forces producing relative motion, between pin 40 and ratchet wheel 42, drive the latter and thereby drive take-up spool 32. As result, floss is drawn through the system to continuously replace floss span 22 as fork 20 reciprocates. As the floss is drawn by take-up spool 32, supply spool spring 30 winds until the clutch slips. Supply spool 26 then slips around spring 30. Thus, the floss is under predetermined constant tension due to the resistance of spring 30.

As described above, the entire system for continuous replacement of floss span 22 is contained in movable flosser head assembly 16. Hence, translation of the relative motion between flosser head assembly 16 and handle assembly 12 drives the progressive replacement of floss span 22.

Flosser head assembly 16 is preferably reciprocated at a frequency high enough (for example, ten cycles per second) such that when floss span 22 encounters resistance in a tight interdental gap, floss span 22 will be reciprocated relative to the gap rather than reciprocating handle assembly 12. As a result, floss span 22 can saw its way through the gap.

During use, a floss loop can be formed part-way around a tooth under tension to enable flossing around the tooth as the floss reciprocates. When the loop is released, spring 30 immediately rewinds the slack to maintain normal tension on the floss.

Flosser head assembly 16 may be interchanged with a toothbrush head on handle assembly 12. The expedient head replacement capability also allows multiple members of a household to use personal flosser heads and toothbrush heads on a common handle.

Figure 4:
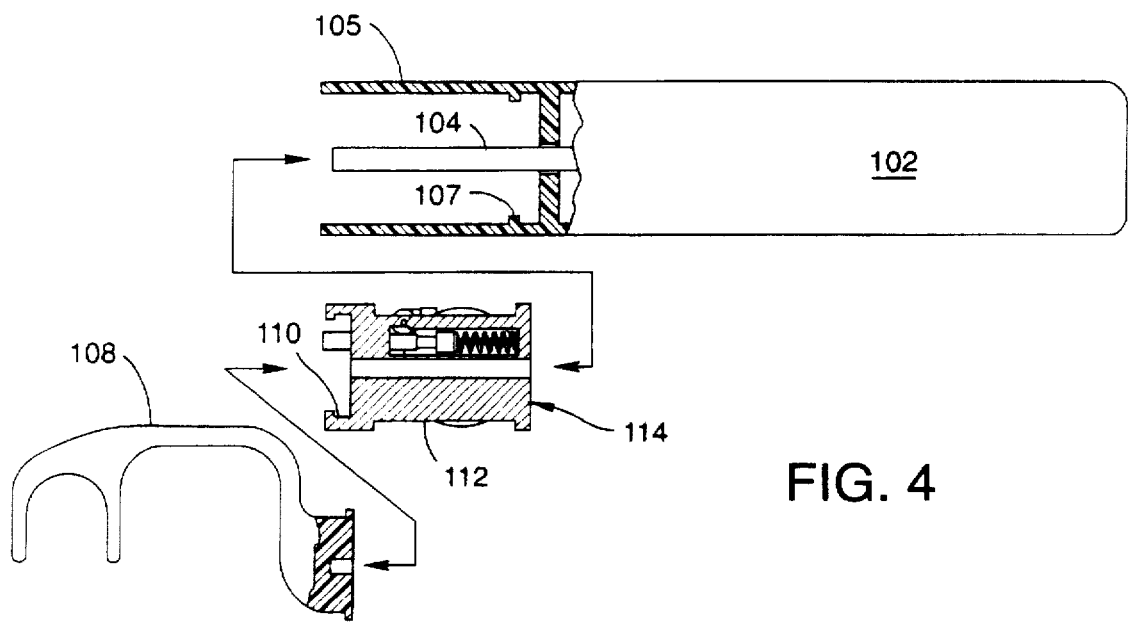
FIG. 4 is a side view, partly in section, of another preferred flosser head partly disassembled and disconnected from a driver.
Figure 5:
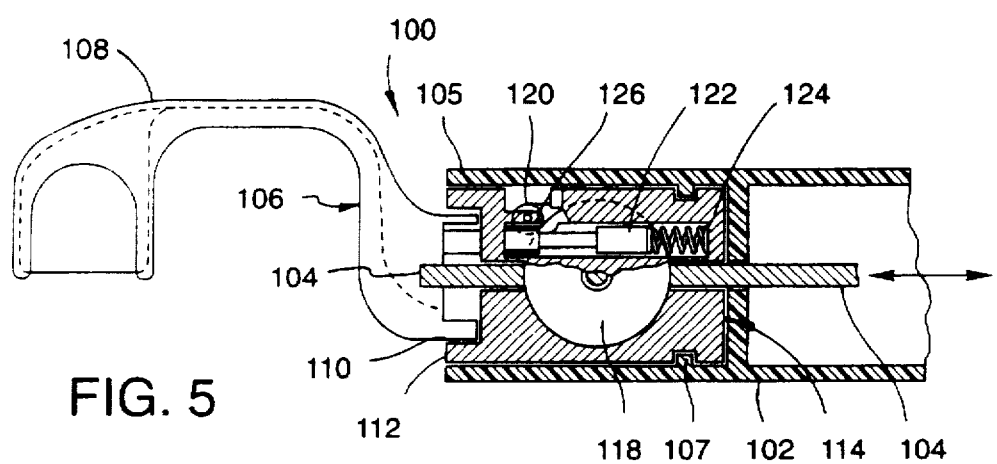
FIG. 5 is a side view, in section, of the flosser head of FIG. 4 connected to the driver.
Figure 6:
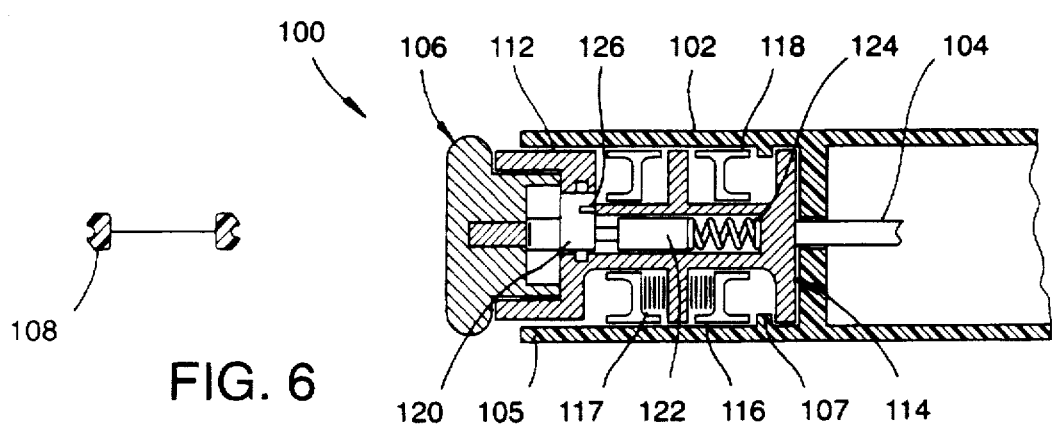
FIG. 6 is a top view, in section, of the flosser head of FIG. 4 connected to the driver.

Another preferred dental cleaner 100 is shown in FIGS. 4–6. Dental cleaner 100 is similar to dental cleaner 10 except as explained hereinafter. Included is a handle assembly 102 which is a conventional motorized toothbrush driver. A drive shaft 104 reciprocates axially relative to handle assembly 102 when a motor (not shown) housed within handle assembly 102 is energized.

A flosser head assembly 106 is detachably connectable to handle assembly 102 by being inserted in an open-end anterior portion 105 of handle assembly 102. A conventional lock 107, such as a twist-lock or snap-lock retains flosser head assembly 106 in handle assembly 102.

Flosser head assembly 106 comprises a fork member 108 slidably supported to telescope in and out of a cavity 110 within a frame 112 of a floss supply and retrieval unit 114. Drive shaft 104 is received in a bore in a posterior portion of fork member 108 and is friction-connected therein. A conventional twist-lock (not shown) is an alternative method of connecting fork member 108 and drive shaft 104. When drive shaft 104 reciprocates, so does fork member 108, in and out of cavity 110. Floss supply and retrieval unit 114, however, remains in place as fork member 108 reciprocates.

Floss supply and retrieval unit 114 includes a floss supply spool 116 (FIG. 6), a supply spool torsion spring 117, a floss take-up spool 118, a ratchet wheel 120 (FIG. 5), a ratchet drive pin 122, a return spring 124, and a pawl 126, all being supported to operate similar to equivalent components of dental cleaner 10. A notable difference, however, is that pin 122 extends anteriorly of frame 112 and is urged by spring 124 to engage the posterior portion of fork member 108. Thus, reciprocating fork member 108, in concert with spring 124, reciprocates pin 122 thereby driving ratchet wheel 120 and take-up spool 118.

Therefore, in this case, the floss supply and retrieval unit 114 is connected to handle assembly 102 wherein fork member 108 is movably supported to reciprocate relative to handle assembly 102 and floss supply and retrieval unit 114. Translation of the relative motion between fork member 108 and handle assembly 102 drives the progressive replacement of the floss span.

The flosser head assembly 106 may be expediently replaced on a common handle with personal flosser heads and toothbrush heads of other members of a household.

While the above description contains many specificities, these should not be construed as limitations on the scope of the invention, but rather as an exemplifications of preferred embodiments. Those skilled in the art will envision other possible variations that are within its scope. Accordingly, the scope of the invention should be determined not by the embodiments illustrated, but by the appended claims and their legal equivalents.

What is claimed is:

1. A dental cleaner comprising:
   a handle having a drive shaft axially reciprocable relative to the handle;
   a fork connected to the drive shaft and movably supported thereon, the fork having a pair of spaced tines for movably supporting a floss span therebetween, the span being longitudinally aligned with the handle; and
   a floss span replacing system for automatically replacing the floss span while flossing teeth.

2. The dental cleaner as defined in claim 1, wherein the floss span replacing system is driven by relative motion between the fork and handle.

3. The dental cleaner as defined in claim 1, wherein the fork is movably supported and the floss span replacing system is connected to the handle, the floss span replacing system being driven by relative motion between the fork and handle.

4. The dental cleaner as defined in claim 1, wherein the floss span replacing system includes a spring for tensioning the floss span.

5. The dental cleaner as defined in claim 1, wherein the fork is supported for pivotal movement about a longitudinal axis of the handle.

6. The dental cleaner as defined in claim 1, wherein each of the fork and the floss span replacing system is detachably connectable to the handle for expedient replacement by a user.

7. A dental cleaner comprising:
   a handle;
   a fork connected to the handle, the fork having a pair of spaced tines for movably supporting a floss span therebetween, the span being longitudinally aligned with the handle; and
   a floss span replacing system comprising a rotatably supported spool for holding floss and a spring connected to the spool for urging rotation of the spool in a floss winding direction to create tension across the floss span, for automatically replacing the floss span while flossing teeth.

8. The dental cleaner as defined in claim 7, wherein the floss span replacing system further comprises a floss take-up spool for winding used floss.

9. The dental cleaner as defined in claim 8, wherein the floss span replacing system is connected to the fork and reciprocated relative to the handle to advance the floss.

10. A dental cleaner comprising:
    a handle;
    a fork connected to the handle, the fork having a pair of spaced tines for movably supporting a floss span therebetween; and
    floss span replacing system connected to the handle and having a ratchet driven by relative motion between the fork and handle for automatically progressively advancing the floss span while flossing teeth to replace the span.

11. The dental cleaner as defined in claim 10, wherein the fork and the floss span replacing system are detachably connectable to the handle for expedient replacement by a user.

12. The dental cleaner as defined in claim 11, wherein the fork is movably supported and the handle includes a fork drive for reciprocating the fork longitudinally to the floss span.

13. A dental cleaner comprising:

a motorized toothbrush handle; and a flosser head detachably connectable to the handle, the flosser head having a pair of spaced tines for movably supporting a floss span therebetween and a floss span replacing system for automatically replacing the floss span while flossing teeth, wherein the floss span replacing system includes a ratchet and a rotatably supported floss take-up spool, the ratchet driving the floss take-up spool.

14. The dental cleaner as defined in claim 13, wherein the floss span is supplied by a rotatably supported floss supply spool which is biased by a spring in a floss winding direction thereby creating tension in the span.

15. The dental cleaner as defined in claim 14, wherein the spring is arranged to wind when force is applied to the floss span thereby yielding floss to the span for flossing around a user tooth.

16. The dental cleaner as defined in claim 15, wherein a clutch is connected to the spool for allowing the spool to yield floss beyond the amount of yield of the spring.

17. A flosser head for use with a motorized toothbrush driver comprising:

a fork having a pair of spaced tines for supporting a span of floss therebetween, the fork being capable of coupling to the toothbrush driver, and a floss replacing system for automatically replacing the span of floss with fresh floss, wherein the fork and the floss replacing system are driven by the toothbrush driver.

18. A method of providing an automated dental flosser comprising the steps of:

coupling a flosser head to a motorized toothbrush driver, the flosser head having a fork with a pair of spaced tines for supporting a span of floss therebetween, the fork being driven in a reciprocating motion by the toothbrush driver; and providing a floss replacing system within the flosser head for automatically replacing the span of floss with fresh floss, the floss replacing system being driven by the toothbrush driver.

19. The method of claim 18, wherein the fork is reciprocated at least ten cycles per second.

* * * * *